US00PP29062P2

(12) United States Plant Patent
Sorensen

(10) Patent No.: US PP29,062 P2
(45) Date of Patent: Mar. 6, 2018

(54) ***EUPHORBIA* PLANT NAMED 'FL 854 1'**

(50) Latin Name: *Euphorbia milii*
Varietal Denomination: FL 854 1

(71) Applicant: Lilly Irene Sorensen, Vester Skerninge (DK)

(72) Inventor: Lilly Irene Sorensen, Vester Skerninge (DK)

(73) Assignee: Florilis ApS, Vester Skerninge (DK)

( * ) Notice: Subject to any disclaimer, the term of this patent is extended or adjusted under 35 U.S.C. 154(b) by 0 days.

(21) Appl. No.: 15/530,389

(22) Filed: Jan. 7, 2017

(51) Int. Cl.
*A01H 5/02* (2006.01)

(52) U.S. Cl.
USPC ..... Plt./302

(58) Field of Classification Search
USPC ..... Plt./302
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Euphorbia* plant named 'FL 854 1', characterized by its broadly upright and mounded plant habit; moderately vigorous growth habit; freely branching habit; dark green-colored leaves; freely flowering habit; large inflorescences with dark red-colored flower bracts; and good post-production longevity.

2 Drawing Sheets

Botanical designation: *Euphorbia milii.*
Cultivar denomination: 'FL 854 1'.

BACKGROUND OF THE INVENTION

The present invention relates to a new and distinct cultivar of *Euphorbia* plant, botanically known as *Euphorbia milii*, commonly referred to as Crown-of-Thorns and hereinafter referred to by the cultivar name 'FL 854 1'.

The new *Euphorbia* plant is a product of a planned breeding program conducted by the Inventor in Odense, Denmark. The objective of the program is to create and develop new *Euphorbia* plants with compact, upright and mounded plant habit and large flower bracts.

The new *Euphorbia* plant originated from a cross-pollination made by the Inventor in August, 2013 in Odense, Denmark of a proprietary selection of *Euphorbia milii* identified as code designation Fl 525 1, not patented, as the female, or seed, parent with a proprietary selection of *Euphorbia milii* identified as code designation 629 1, not patented, as the male, or pollen, parent. The new *Euphorbia* plant was discovered and selected by the Inventor as a single flowering plant within the progeny of the stated cross-pollination in a controlled greenhouse environment in Odense, Denmark on Jun. 16, 2014.

Asexual reproduction of the new *Euphorbia* plant by terminal vegetative cuttings in a controlled greenhouse environment in Odense, Denmark since June, 2014 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'FL 854 1'. These characteristics in combination distinguish 'FL 854 1' as a new and distinct *Euphorbia* plant:

1. Broadly upright and mounded plant habit.
2. Moderately vigorous growth habit.
3. Freely branching habit.
4. Dark green-colored leaves.
5. Freely flowering habit.
6. Large inflorescences with dark red-colored flower bracts.
7. Good post-production longevity.

Plants of the new *Euphorbia* differ primarily from plants of the female parent selection in growth rate as plants of the new *Euphorbia* grow faster than plants of the female parent selection.

Plants of the new *Euphorbia* differ primarily from plants of the male parent selection in flower bract color as plants of the male parent selection have pale red-colored flower bracts.

Plants of the new *Euphorbia* can be compared to plants of the *Euphorbia milii* 'Karola', not patented. In side-by-side comparisons, plants of the new *Euphorbia* differ primarily from plants of 'Karola' in inflorescence size as plants of the new *Euphorbia* have larger inflorescences than plants of 'Karola'.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph on the first sheet is a side perspective view of a typical flowering plant of 'FL 854 1' grown in a container.

The photograph on the second sheet are close-up views of the upper and lower surfaces of typical leaves and inflorescences of 'FL 854 1'.

DETAILED BOTANICAL DESCRIPTION

Plants used in the aforementioned photographs and described herewith in detail were grown during the autumn in 17-cm containers in glass-covered greenhouse in Rijnsburg, The Netherlands and under cultural practices typical of commercial *Euphorbia* production. During the production of the plants, day temperatures ranged from 20° to 28° C. and night temperatures ranged from 18° to 22° C. Plants were 3.2 months old when the photographs and the description were taken. In the following description, color references are made to The Royal Horticultural Society Colour Chart, Sixth Edition, 2015, except where general terms of ordinary dictionary significance are used.

Botanical classification: *Euphorbia milii* 'FL 854 1'.

Parentage:

- *Female, or seed, parent*.—Proprietary selection of *Euphorbia milii* identified as code designation FL 525 1, not patented.
- *Male, or pollen, parent*.—Proprietary selection of *Euphorbia milii* identified as code designation 629 1, not patented.

Propagation:

- *Type*.—Terminal vegetative cuttings.
- *Time to initiate roots, summer*.—About three weeks at temperatures about 24° C.
- *Time to initiate roots, winter*.—About four weeks at temperatures about 22° C.
- *Time to produce a rooted young plant, summer*.—About five weeks at temperatures ranging from 20° C. to 28° C.
- *Time to produce a rooted young plant, winter*.—About six weeks at temperatures ranging from 20° C. to 24° C.
- *Root description*.—Fine; typically white in color, actual color of the roots is dependent on substrate composition, water quality, fertilizer type and formulation, substrate temperature and physiological age of roots.
- *Rooting habit*.—Moderately freely branching; medium density.

Plant description:

- *Plant habit and form*.—Broadly upright and mounded plant habit; globular in shape; moderately vigorous growth habit.
- *Plant height*.—About 17.7 cm.
- *Plant diameter or spread*.—About 28.8 cm.
- *Lateral branch description*.—Branching habit: Freely branching habit, about eight lateral branches develop per plant. Length: About 7.1 cm. Diameter: About 1.2 cm. Internode length: About 7 mm. Aspect: Upright to about 40° to 60° from vertical. Strength: Moderately strong. Texture and luster: Smooth, moderately to strongly angulate; glabrous; slightly to moderately glossy. Color, developing: Close to 143B to 143C; at the internodes, close to 146A to 146B. Color, developed: Close to 146A to 146B; at the internodes, close to 146A to 146B.
- *Spines*.—At each leaf, there are three sharp spines, one larger than the other two smaller spines; with development, smaller spines abscise. Length, larger spine: About 1.2 cm. Width, larger spine, at base: About 4 mm. Length, smaller spines: About 4 mm. Width, smaller spines, at base: About 1.5 mm. Texture: Smooth, glabrous. Color: Close to 200B to 200C; with development, color becoming closer to N199A and 199B.
- *Leaves*.—Arrangement: Alternate, simple. Length: About 11.9 cm. Width: About 4.8 cm. Shape: Narrowly obovate. Apex: Obtuse to very broad acute or shallowly retuse. Base: Cuneate. Margin: Entire; slightly to moderately undulate. Venation pattern: Pinnate. Texture and luster, upper surface: Smooth, glabrous; matte. Texture and luster, lower surface: Smooth, glabrous; slightly glossy. Color: Developing leaves, upper surface: Close to 144A. Developing leaves, lower surface: Close to between 143C and 144B. Fully developed leaves, upper surface: Close to NN137A; venation, close to 137B. Fully developed leaves, lower surface: Close to between 138A and 146B; venation, close to 144C. Petioles: Length: About 5 mm. Diameter: About 4 mm. Strength: Strong. Texture and luster, upper and lower surfaces: Smooth, glabrous; slightly glossy. Color, upper surface: Close to 143B. Color, lower surface: Close to 144C.

Inflorescence description:

- *Inflorescence type and habit*.—Inflorescences are compound cymes of cyathia with two showy flower bracts; inflorescences face slightly to moderately outwardly; freely flowering habit with about ten open inflorescences per plant at one time.
- *Inflorescence diameter*.—About 7.1 cm.
- *Inflorescence height*.—About 5.5 cm.
- *Fragrance*.—None detected.
- *Natural flowering season*.—Plants typically flower during the late autumn and winter in Japan; about 14 weeks are required to produce a flowering plant.
- *Post-production longevity*.—Good post-production longevity; plants of the new *Euphorbia* maintain good substance and bract color for about three to four weeks.
- *Flower buds*.—Length: About 1 cm. Diameter: About 5 mm. Shape: Oblong. Texture and luster: Smooth, glabrous; slightly glossy. Color: Close to 145B.
- *Flower bracts*.—Quantity per inflorescence: Two. Length: About 3.1 cm. Width: About 3.6 cm. Shape: Rounded reniform; sessile. Apex: Retuse. Base: Reniform to truncate. Margin: Entire. Aspect: Perpendicular to peduncle axis. Texture and luster, upper and lower surfaces: Smooth, glabrous; matte. Color: Developing bracts, upper surface: Close to 39A. Developing bracts, lower surface: Close to 48A to 48B. Fully expanded bracts, upper surface: Close to 45C; color does not fade with development. Fully expanded bracts, lower surface: Close to 45D; color does not fade with development.
- *Cyathia*.—Quantity per cyme: About three. Length, individual cyathium: About 7 mm. Width, individual cyathium: About 7 mm. Shape, individual cyathium:

Obovate; sessile. Texture and luster, inner and outer surfaces: Smooth, glabrous; matte. Color: When developing, inner and outer surfaces: Close to 145B. Fully developed, inner and outer surfaces: Close to between 145B and 150B.

*Nectaries*.—Quantity per cyathium: About six. Length: About 2 mm. Width: About 3 mm. Shape: Reniform. Texture and luster, inner surface: Smooth, glabrous; glossy. Texture and luster, outer surface: Smooth, glabrous; matte. Color: When developing, inner surface: Close to between 22A and N167C. When developing, outer surface: Close to 162B and 162C. Fully developed, inner surface: Close to 167A. Fully developed, outer surface: Close to 163B to 163C.

*Peduncles*.—Length: About 6 cm. Diameter: About 3 mm. Strength: Strong. Aspect: About 60° from lateral branch axis. Texture and luster: Smooth, glabrous; moderately glossy. Color: Close to 144B tinged with close to 185A.

*Pedicels*.—Length: About 2.5 cm. Diameter: About 2.5 mm. Strength: Moderately strong. Aspect: About 10° to 50° from peduncle axis. Texture and luster: Smooth, glabrous; moderately glossy. Color: Close to 144B tinged with close to 185A.

*Reproductive organs*.—Stamens: Quantity per cyathium: About six. Filament length: About 2 mm. Filament color: Close to 150D. Anther shape: Club-shaped. Anther length: About 1 mm. Anther color: Close to 40A. Amount of pollen: None observed. Pistils: Quantity per cyathium: One. Pistil length: About 3 mm. Style length: About 2 mm. Style color: Close to 47D. Stigma diameter: About 2 mm. Stigma shape: Club-shaped. Stigma color: Close to N186C. Ovary color: Close to 144C.

*Seeds and fruits*.—Seed and fruit production has not been observed on plants of the new *Euphorbia*.

Disease & pest resistance: Plants of the new *Euphorbia* have not been shown to be resistant to pathogens and pests common to *Euphorbia* plants.

Temperature tolerance: Plants of the new *Euphorbia* have been observed to tolerate high temperatures about 35° C. and to be suitable for USDA Hardiness Zones 10 to 12.

It is claimed:

1. A new and distinct *Euphorbia* plant named 'FL 854 1' as illustrated and described.

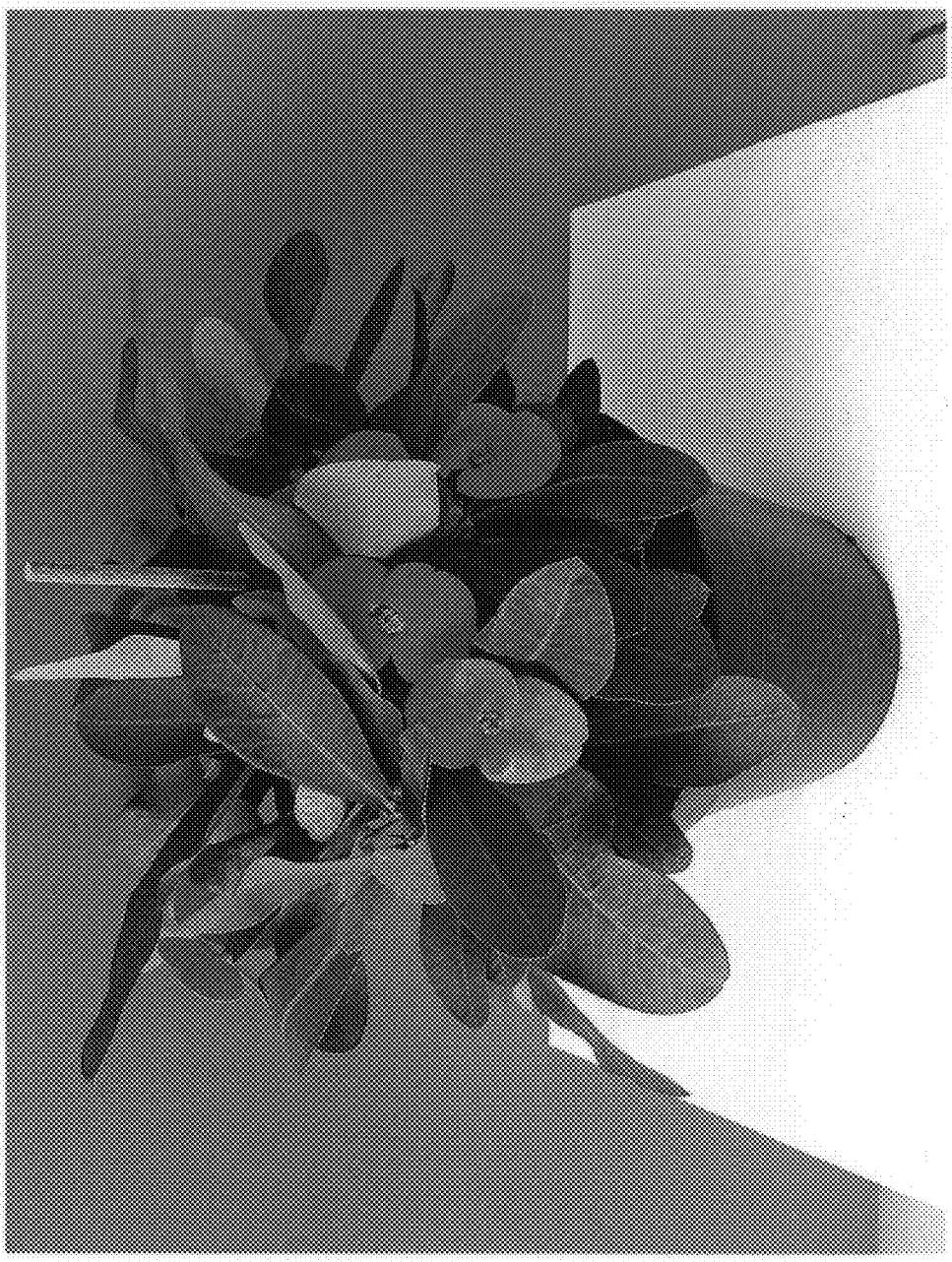

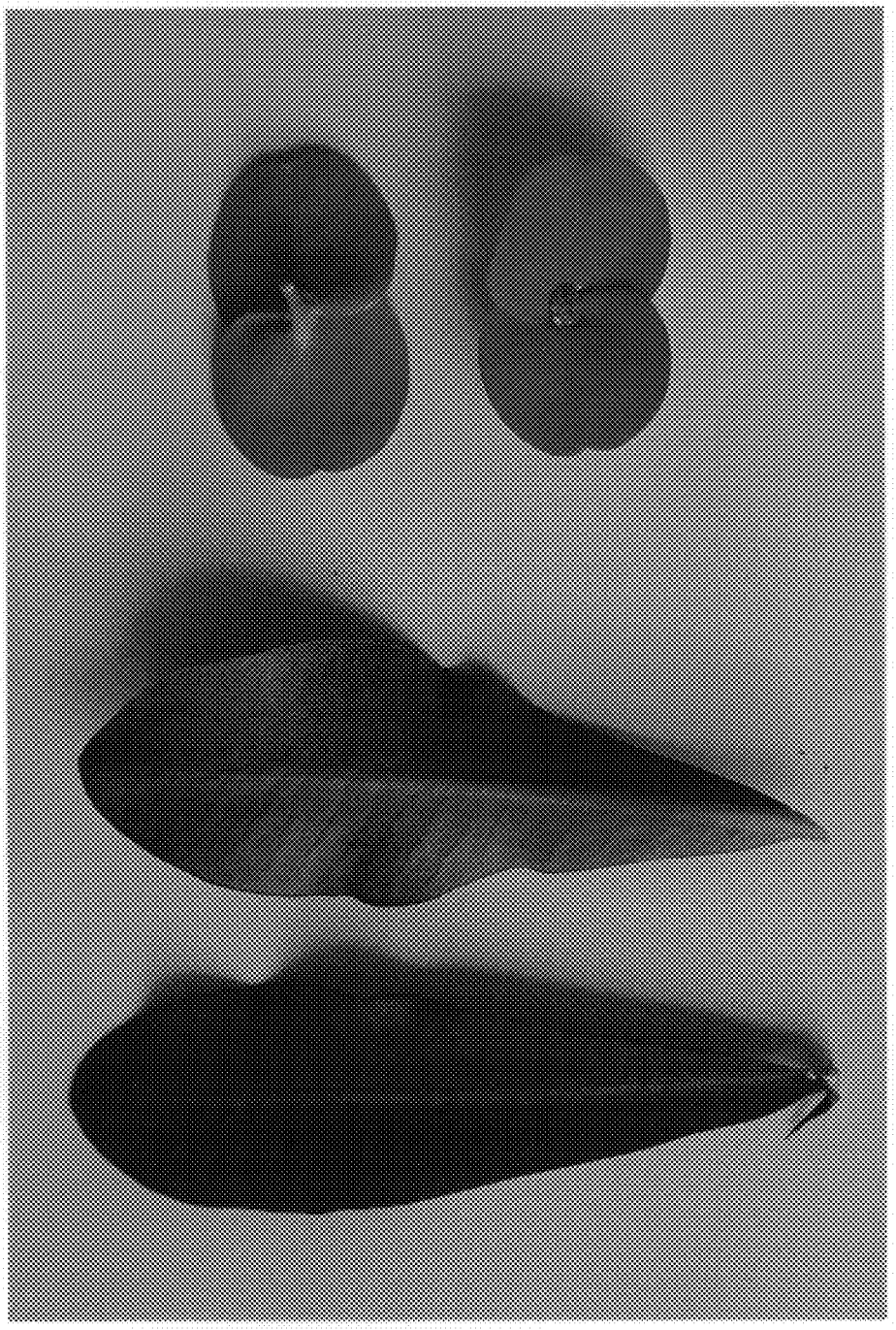

* * * * *